United States Patent [19]
Breton et al.

[11] Patent Number: 6,146,636
[45] Date of Patent: Nov. 14, 2000

[54] SUBSTANCE P ANTAGONISTS COMPRISING ROSACEAE PLANT EXTRACTS

[75] Inventors: Lionel Breton, Versailles; Nathalie Pineau, Poitiers, both of France

[73] Assignee: Societe l'Oreal S.A., Paris, France

[21] Appl. No.: 09/157,983

[22] Filed: Sep. 22, 1998

[30] Foreign Application Priority Data

Sep. 22, 1997 [FR] France .................................. 97 11761

[51] Int. Cl.[7] .............................. A61K 7/00; A61K 35/78
[52] U.S. Cl. ......................................... 424/195.1; 424/401
[58] Field of Search ................................ 424/195.1, 401; 514/886, 887

[56] References Cited

U.S. PATENT DOCUMENTS 5,932,215  8/1999  De Laccharriere et al. ........ 424/158.1

FOREIGN PATENT DOCUMENTS

| | | |
|---|---|---|
| 0592220 | 4/1994 | European Pat. Off. . |
| 2035747 | 12/1970 | France . |
| 2366836 | 5/1978 | France . |
| 2690344 | 10/1993 | France . |
| 2729859 | 8/1996 | France . |
| 2736263 | 1/1997 | France . |
| 2753466 | 5/1979 | Germany . |
| 196 11 078 | 9/1996 | Germany . |
| 403188014 | 8/1991 | Japan . |

OTHER PUBLICATIONS

Database WPI, Section Ch. Week 9816, Derwent Publications.
Database WPI, Section Ch, Week 9729, Derwent Publications.
Database WPI, Section Ch, Week 9616, Derwent Publications.
Database WPI, Section Ch, Week 9048, Derwent Publications.
Database WPI, Section Ch, Week 8444, Derwent Publications.
Database WPI, Section Ch, Week 9415, Derwent Publications.
Database Biosis Biosciences Infor. Serc.; Abstract No. 88:378016.
Database WPI, Section Ch, Week 9538, Derwent Publications.

*Primary Examiner*—Thurman K. Page
*Assistant Examiner*—Lakshmi Channavajjala
*Attorney, Agent, or Firm*—Burns, Doane, Swecker & Mathis, L.L.P.

[57] ABSTRACT

Disease states, disorders, conditions or afflictions manifesting excessive synthesis and/or release of substance P are therapeutically treating by administering to individuals in need of such treatment, an effective substance P antagonist amount of at least one extract of at least one plant of the Rosaceae family.

11 Claims, No Drawings

SUBSTANCE P ANTAGONISTS COMPRISING ROSACEAE PLANT EXTRACTS

CROSS-REFERENCE TO PRIORITY APPLICATION

This application claims priority under 35 U.S.C. §119 of FR-97/11761, filed Sep. 22, 1997, assigned to the assignee hereof and hereby expressly incorporated by reference.

CROSS-REFERENCE TO COMPANION APPLICATION

Our application Ser. No. 09/157,982, filed concurrently herewith and also assigned to the assignee hereof.

BACKGROUND OF THE INVENTION

1. Technical Field of the Invention

The present invention relates to novel substance P antagonist compositions comprising at least one extract of at least one plant of the Rosaceae family.

This invention also relates to the administration of at least one extract of at least one plant of the Rosaceae family, as the active species or agent for treating disorders associated with an excessive synthesis and/or release of substance P.

The present invention also relates to the use of the subject extracts/compositions for treating sensitive human skins.

2. Description of the Prior Art

There exist, in mammals, polypeptides belonging to the family of tachykinins which induce rapid contractions on the smooth muscle fibers. Among the compounds of this family, representative are β-neurokinin, α-neurokinin and substance P.

Substance P is a polypeptide chemical component (undecapeptide), produced and released by a nerve ending. The location of substance P is specific to the neurons, both in the central nervous system and in the organs at the periphery. Thus, numerous organs or tissues receive afferences of substance P-bearing neurons; these are, especially, the salivary glands, the stomach, the pancreas, the intestine (in the latter, the distribution of substance P is superposed on the intrinsic Meissner's and Auerbach's nerve plexus), the cardiovascular system, the thyroid gland, the skin, the iris and the ciliary bodies, the bladder and obviously the central and peripheral nervous systems.

By virtue of the ubiquitous distribution of substance P, numerous disorders are associated with an excessive synthesis and/or release of substance P.

Substance P is involved, particularly, in the transmission of pain and in diseases of the central nervous system (for example anxiety, psychoses, neuropathies, neurodegenerative disorders of the type comprising senile dementia of Alzheimer, dementia of AIDs sufferers, Parkinson's disease, Down's syndrome, Korsakoff's syndrome, multiple sclerosis, schizophrenia), in respiratory diseases (such as for example bronchopneumonia) and inflammatory diseases (such as for example rheumatoid arthritis), in allergic syndromes (such as for example asthma, allergic rhinitis, allergic pharyngitis, urticaria, eczematous dermatitis), in gastrointestinal diseases (such as for example ulcers, colitis, Crohn's disease), in skin disorders (such as for example psoriasis, pruriginous diseases, herpes, photodermatosis, atopic dermatitis, contact dermatitis, lichen, prurigo, pruritus, erythema, in particular solar erythema, insect bites), in fibrosis and other collagen maturation disorders (such as for example scleroderma), in cardiovascular disorders, vasospastic disorders (such as for example migraine, Reynaud's disease), in immunological disorders, in disorders of the urinary tract (such as for example incontinence, cystitis), in rheumatic diseases, in some dermatological diseases (such as eczema) and in ophthalmological conditions (such as for example conjunctivitis, uveitis, ocular pruritus, ocular pain, irritations).

The administration of a substance P antagonist is one of the therapeutic alternatives which is effective in all of the aforementioned conditions and afflictions.

By "substance P antagonist" is intended any compound or species capable of inhibiting partially, or even completely, the biological effect of substance P.

In particular, for a substance to be recognized as a substance P antagonist, it should induce a coherent pharmacological response (including or otherwise its attachment to the substance P receptor), especially in one of the following tests:

(a) the antagonist substance should reduce the extravasation of plasma across the vascular wall induced by capsaicin or by an antidromic nerve stimulation, and/or (b) the antagonist substance should cause inhibition of the contraction of the smooth muscles induced by the administration of substance P.

To date, substance P antagonists have been administered to treat the disorders indicated above. Compare, for example, U.S. Pat. No. 4,472,305, U.S. Pat. No. 4,839,465, EP-A-101929, EP-A-333174, EP-A-336230, EP-A-394989, EP-A-443132, EP-A-498069, EP-A-515681, EP-A-517589, WO-A-92/22569, GB-A-2216529, EP-A-360390, EP-A-429366, EP-A-430771, EP-A-499313, EP-A-514273, EP-A-514274, EP-A-514275, EP-A-514276, EP-A-520555, EP-A-528495, EP-A-532456, EP-A-545478, EP-A-558156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116, EP-A-522808 and WO-A-93/01165.

However, the aforesaid prior art neither discloses nor suggests that an extract of at least one plant of the Rosaceae family elicits a substance P-antagonizing activity as defined above and therefore would be useful as an active ingredient for treating the disorders indicated above.

Plants of the Rosaceae family are principally used for their aromatic and ornamental properties.

In the prior art, plants of the Rosaceae family have been utilized in compositions for the treatment of urogenital diseases (FR-76/36295), in lightening cosmetic compositions (JP-08208451) or in compositions for protecting against ultraviolet radiation (EP-A-781544), for the preparation of antioxidant compounds (EP-A-94/401669), or, alternatively, for the preparation of antimicrobial and/or insecticidal compounds for the protection of plants (DE-4,327,792).

Heretofore, the substance P-antagonizing activity of at least one plant of the Rosaceae family was unknown.

SUMMARY OF THE INVENTION

Unexpectedly, it has now been determined that at least one extract of at least one plant of the Rosaceae family exhibits substance P antagonist actively and can thus be administered as a substance P antagonist.

Accordingly, the present invention features substance P antagonist compositions comprising an effective amouknt of at least one extract of at least one plant of the Rosaceae family.

DETAILED DESCRIPTION OF BEST MODE AND SPECIFIC/PREFERRED EMBODIMENTS OF THE INVENTION

By "active ingredient" (or agent or species) is intended any molecule or extract capable of modifying or of modulating the functioning of at least one given biological system.

The extract of at least one plant of the Rosaceae family may be any extract prepared from any plant material derived from at least one plant of the Rosaceae family.

Thus, the extract of at least one plant of the Rosaceae family according to the invention may be obtained from plant material derived from a whole plant, or from a plant portion such as the leaves, stems, flowers, petals, roots or, alternatively, from undifferentiated cells.

By "undifferentiated plant cell" is intended any plant cell exhibiting none of the characteristics of a specific specialization and capable of living or remaining viable by itself and not in dependence on other cells. These undifferentiated plant cells may be capable, under the influence of an induction, of any differentiation consistent with their genome.

According to the technique of culture selected, and in particular according to the selected culture medium, it is possible to obtain, from the same explant, undifferentiated plant cells having different characteristics.

Preferably according to the invention, petals are employed.

The extract of at least one plant of the Rosaceae family may be any extract prepared from any plant material derived from at least one plant of the Rosaceae family cultured in vivo or derived from in vitro culture.

By "in vivo" culture is intended any culture of a conventional type, namely, in the soil, outdoors or in a greenhouse, or, alternatively, soil-free culture.

By "in vitro culture" is intended the range of techniques known to this art which makes it possible to artificially obtain a plant or a portion of a plant. The selection pressure imposed by the physicochemical conditions during the growth of plant cells in vitro makes it possible to obtain a plant material which is standardized and available throughout the year, contrary to the plants cultured in vivo.

Preferably according to the invention, a plant derived from in vivo culture is used.

Any extraction technique known to this art may be used to prepare the extract contained in the compositions according to the invention.

Exemplary are those utilizing, in particular, aqueous or alcoholic extracts, or extracts obtained from an organic solvent.

By "aqueous solvent" is intended any solvent consisting completely or partly of water. Exemplary are water itself, aqueous/alcoholic solvents in any proportion or, alternatively, solvents comprising water and a compound such as propylene glycol in any proportion.

Among the alcoholic solvents, ethanol is particularly representative.

An extract prepared by the method described in French patent application No. 95-02379, assigned to the assignee hereof, is also exemplary.

Thus, in a first step, the plant material is ground in an aqueous solution at cold temperature, in a second step, the particles in suspension are removed from the aqueous solution derived from the first step, and, in a third step, the aqueous solution derived from the second step is sterilized. This aqueous solution corresponds to the extract.

Moreover, the first step may advantageously be replaced by a simple operation of freezing the plant tissues (for example at −20° C.), followed by an aqueous extraction comprising the second and third steps described above.

Regardless of the mode of preparation according to the invention, subsequent steps intended to promote preservation and/or stabilization may be included without as a result modifying the actual nature of the extract. Thus, for example, the extract obtained may be freeze-dried by any conventional freeze-drying method. A powder is thus obtained which may be used directly or, alternatively, mixed in an appropriate solvent before use.

Preferably according to the invention, an aqueous extract and even more preferably an extract prepared with a solvent composed of water and of propylene glycol, such as for example Herbasol® marketed by COSMETOCHEM, is used.

Examples of disorders associated with an excessive synthesis and/or release of substance P were set forth hereinbefore.

The present invention thus features formulating an effective amount of an extract of at least one plant of the Rosaceae family into a cosmetic/pharmaceutical composition, the extract or the composition being well suited for treating disorders associated with an excessive synthesis and/or release of substance P.

Thus, according to one specific embodiment of the invention, cosmetic/pharmaceutical compositions comprising an effective amount of an extract of at least one plant of the Rosaceae family are used for treating skin disorders, inflammation, allergic syndromes, pain, collagen maturation disorders, disorders of the central nervous system, respiratory disorders, gastrointestinal disorders, fibroses, cardiovascular disorders, vasospastic disorders, immunological disorders or disorders of the urinary tract, rheumatic diseases or certain ophthalmological conditions.

In respect of skin disorders, it is known that certain skins are more "sensitive" than others. However, the symptoms of sensitive skins were, to date, poorly characterized and the problem of these skins was, as a result, poorly defined. The exact process involved in the sensitization of the skin was unknown. Certain researchers considered that a sensitive skin was a skin which reacted to cosmetic products, others that it was a skin which reacted to a variety of external factors, not necessarily associated with cosmetic products. Sensitive skin was also synonymous with allergic skin.

Tests have now been developed to better understand sensitive skins, for example tests with lactic acid and DMSO which are known irritant substances: see, for example, the article by K. Lammintausta et al., *Dermatoses*, 36, pages 45–49 (1988); and the article by T. Agner and J. Serup, *Clinical and Experimental Dermatology*, 14, pages 214–217 (1989).

Because of the lack of knowledge about the characteristics of sensitive skins, it was, to date, very difficult or even impossible to treat them. Indeed, they were treated indirectly, for example by limiting, in cosmetic or dermatological compositions, incorporation of products normally irritating to the skin, such as surfactants, preservatives, perfumes, as well as certain cosmetic or dermatological active agents.

After numerous clinical tests, the assignee hereof has been able to determine the symptoms linked to sensitive skins. These symptoms are in particular subjective signs, which are essentially dysaesthetic sensations. By "dysaesthetic sensations" are intended more or less painful sensations felt in a skin area, such as prickling, formication, itching or pruritus, burns, inflammation, discomfort, stabbing pain, etc.

Thus, it has now been shown, in addition, that a sensitive skin was not an allergic skin. Indeed, an allergic skin is a skin which reacts to an external agent, an allergen, which triggers an allergic reaction. It is an immunological process which occurs only when an allergen is present and which only affects sensitized subjects. The essential characteristic of sensitive skin is, according to the assignee hereof, on the contrary, a mechanism of response to external factors, which may affect any individual, even though the individuals with so-called sensitive skin react thereto more quickly than others. This mechanism is not immunological; it is aspecific.

Hence, it has been found that sensitive skins could be separated into two principal clinical states, the irritable and/or reactive skins, and the intolerant skins.

An irritable and/or reactive skin is a skin which reacts by pruritus, namely, by itching, or by prickling, to various factors such as the environment, emotions, food, wind, rubbing, razor, soap, surfactants, hard water having a high chalk concentration, temperature variations or wool. In general, these signs are associated with a dry skin with or without dartre, or with a skin exhibiting an erythema.

An intolerant skin is a skin which reacts by sensations of inflammation, stabbing pain, formication and/or blotches, to various factors such as the environment, emotions, food and certain cosmetic products. In general, these signs are also associated with a hyperseborrhoeic skin or with a skin with acne, with or without dartre, and with an erythema.

"Sensitive" scalps have a more univocal clinical semiology: the sensations of pruritus and/or of prickling and/or of inflammation are essentially triggered by local factors such as rubbing, soap, surfactants, hard water having a high chalk concentration, shampoos or lotions. These sensations are also sometimes triggered by factors such as the environment, emotions and/or food. An erythema and a hyperseborrhoea of the scalp, as well as a dandruff condition, are frequently associated with the above signs.

Furthermore, in certain anatomical regions such as the large skin-folds (inguinal, genital, axillary, popliteal, anal or submammary regions, skin-fold of the elbow) and the feet, the sensitive skin results in pruriginous sensations and/or dysaesthetic sensations (inflammation, prickling) linked, in particular. to sweat, rubbing, wool, surfactants, certain cosmetic preparations, hard water having a high chalk concentration and/or temperature variations.

To determine if a skin is sensitive or not, the assignee hereof has developed a test. Indeed, after having carried out a large number of tests with the goal of defining a sensitive skin, it was surprisingly found that there was a link between individuals with sensitive skin and those who reacted to a topical application of capsaicin.

The capsaicin test entails applying, over about 4 $cm^2$ of skin, 0.05 ml of a cream comprising 0.075% capsaicin and in noting the appearance of subjective signs caused by this application, such as prickling, burns and itching. In subjects with sensitive skins, these signs appear between 3 to 20 minutes after the application and are followed by the appearance of an erythema which begins at the periphery of the area of application.

To date, capsaicin was used as a medicinal active agent, in particular to treat zona pains. Capsaicin causes a release of the neuropeptides, and in particular of tachykinins which are derived from the nerve endings of the epidermis and of the dermis. It was observed that the physiopathological pattern common to all the conditions of sensitive skins was associated with a high capacity to release tachykinins and more particularly substance P in the skin. The dysaesthetic manifestations which are caused by their release are termed "neurogenic."

Also to date, a link had not been established between substance P and sensitive skin. The clinical signs of sensitive skin are essentially subjective: prickling, formication, pruritus, stabbing pain, inflammation, and they are sometimes combined with erythemas. These signs are due to aspecific external factors. The symptoms appear to be essentially restricted to the face, the neck and the scalp, but may also appear over the entire body.

Thus, the assignee hereof has discovered that one of the essential characteristics of sensitive skins is associated with the release of substance P and therefore that the use of substance P antagonists permits eliciting a preventive and/or curative effect on sensitive skin.

To treat sensitive skins, substance P antagonists have been used. It has indeed been observed, surprisingly, that the incorporation of the substance P antagonist into a composition suited for topical use makes it possible to avoid skin irritation and/or dysaesthetic sensations and/or pruritus of the skin.

This invention therefore features, more particularly, the use, as active agent, in a cosmetic/pharmaceutical composition, of an effective amount of at least one extract of at least one plant of the Rosaceae family, the extract or the composition being well suited for treating sensitive skin.

The present invention also features cosmetic/pharmaceutical compositions comprising an effective amount of at least one extract of at least one plant of the Rosaceae family, for preventing and/or combating skin irritations and/or dartres and/or erythemas and/or sensations of inflammation and/or of dysaesthesia and/or pruritus of the skin and/or the mucous membranes.

The Rosaceae family comprises 27 genera including, for example, the genera Agrimonia, Amygdalus, Armeniaca, Cerasus, Malus, Mespilus, Persica, Pirus, Prunus, Rosa, Rubus.

Thus, the Rosaceae extract of the invention is an extract prepared from material derived from at least one plant belonging to a genus selected from among Agrimonia, Amygdalus, Armeniaca, Cerasus, Malus, Mespilus, Persica, Pirus, Prunus, Rosa, Rubus.

Preferably, the plant belongs to the Rosa genus.

The Rosa genus comprises more than 1,000 species including, for example, *Rosa alba, Rosa alpina, Rosa canina, Rosa cinnamonea, Rosa gallica, Rosa repens, Rosa rubrifolia, Rosa rubiginosa, Rosa sempervirens, Rosa spinosissima, Rosa stylosa, Rosa tomentosa* or *Rosa villosa*.

Thus, the plant extract of the Rosa genus of the invention is an extract prepared from material derived from at least one plant belonging to a species selected from among *Rosa alba, Rosa alpina, Rosa canina, Rosa cinnamonea, Rosa gallica, Rosa repens, Rosa rubrifolia, Rosa rubiginosa, Rosa sempervirens, Rosa spinosissima, Rosa stylosa, Rosa tomentosa, Rosa villosa*.

Preferably, the plant belongs to the species *Rosa gallica*.

According to the present invention, the amount of extract of at least one plant of the Rosaceae family formulated into the subject compositions of course depends on the desired effect and can therefore vary widely.

To provide an order of magnitude, the extract is advantageously incorporated in an amount representing from 0.01% to 30% of the total weight of the composition and, preferably, in an amount representing from 0.1% to 20% of the total weight of the composition.

An irritable skin was earlier defined. Skin irritation may have multiple causes. They may be intrinsic causes, linked to deregulation of the physiological mechanisms providing a normal skin. But they may also be extrinsic causes such as irritant compounds which might contact the skin.

Thus, the present invention also features a regime or regimen for reducing skin irritation, comprising topically applying a cosmetic/pharmaceutical composition which contains at least one extract of at least one plant of the Rosaceae family formulated into a cosmetically acceptable medium (vehicle, diluent or carrier) onto the skin, onto the hair and/or onto the mucous membranes.

By "cosmetically/pharmaceutically acceptable medium" is intended compatible with the skin, the scalp, the mucous membranes, the nails and the hair.

The cosmetic treatment of the invention may be carried out by applying the hygiene or cosmetic/pharmaceutical compositions as described above via the usual techniques for administering such compositions. For example: topical application of creams, gels, sera, lotions, makeup removing milks or antisun (sunscreen) compositions to the skin or to dry hair, application of a hair lotion to wet hair, of shampoos, or application of dentifrice to the gums.

Advantageously, at least one extract of at least one plant of the Rosaceae family may be administered in combination with active agents or species which normally elicit irritant effect and which are common in the cosmetic or pharmaceutical field. The presence of a substance P antagonist in the form of at least one extract of at least one plant of the Rosaceae family formulated into a cosmetic or pharmaceutical composition containing a product having an irritant effect makes it possible to greatly attenuate, or even suppress, this irritant effect.

This permits, in addition, increasing the amount of active ingredient exhibiting an irritant effect relative to the amount of active ingredient normally employed, for enhanced efficacy.

This invention more particularly features a composition comprising, in a physiologically acceptable medium, at least one substance eliciting a skin-irritating response and at least one extract of at least one plant of the Rosaceae family.

By "physiologically acceptable medium" is intended compatible with the skin, the scalp, the mucous membranes, the nails and the hair.

In this embodiment of the invention, the extract of at least one plant of the Rosaceae family is an extract as described above.

Exemplary active agents or species promoting an irritant effect include, for example, surfactants (ionic or nonionic), preservatives, organic solvents or active agents such as α-hydroxy acids (citric, malic, glycolic, tartaric, mandelic or lactic acid), β-hydroxy acids (salicylic acid and derivatives thereof), α-keto acids, β-keto acids, retinoids (retinol, retinal, retinoic acid), anthralins (dioxyanthranol), anthranoids, peroxides (especially benzoyl peroxides), minoxidil, lithium salts, antimetabolites, vitamin D and derivatives thereof, hair dyes or colorants (para-phenylenediamine and derivatives thereof, aminophenols), perfuming alcoholic solutions (perfumes, toilet waters, aftershave, deodorants), antiperspirants (certain aluminum salts), depilatory or permanent-waving active agents (thiols), depigmenting active agents (hydroquinone).

The use of a substance P antagonist makes it possible, in particular, to multiply 2- to 10-fold the amount of active ingredient exhibiting an irritant effect relative to the prior state of the art, without experiencing all of the discomforts indicated above. Thus, hydroxy acids may be used up to 50% of the weight of the composition and retinoids up to 5%, by substantially reducing their irritant nature consistent herewith.

It too is known, furthermore, that numerous phenomena of intolerance exist at the level of the skin, of which the symptoms are in particular subjective signs which are essentially dysaesthetic sensations. By dysaesthetic sensations" are intended more or less painful sensations felt in a skin region such as prickling, formication, itching or pruritus, burns, inflammation, discomfort, stabbing pain and the like.

These phenomena may be the consequence of multiple events, of which the most common will be described as irritation or inflammation, but certain of which will be due to physiological causes, such as sensitive skins, or even pathological causes such as, for example, allergy.

However, the sensitive skin may also react by sensations of inflammation, stabbing pain, formication and/or blotches, to various factors such as the environment, emotions or food. In general, these signs are associated with a hyperseborrhoeic skin or a skin with acne, with or without dartres. Here also, these signs are often associated with an erythema.

These phenomena can be generalized to the entire body, but most often they may have well-defined locations such as for example the scalp, the face, the skin folds and the like.

The range of these intolerance phenomena is always linked to a conventional inflammatory process, and more particularly to an inflammatory reaction of the neurogenic type since it involves cutaneous nerve fibers.

An allergic skin is a skin which reacts to an external agent, an allergen, which triggers an allergic reaction. It is therefore a specifically immunological process which occurs only when an allergen is present and which affects only sensitized subjects. On the other hand, the final product of an allergic reaction also results in an acute inflammatory reaction generally associated with an oedema.

Regardless of the phenomenon envisaged, there is a feature common to all these mechanisms which results in an inflammatory reaction, of which the terminal facet can be measured by the release, by the mast cells of the skin, of at least one inflammation mediator such as histamine, serotonin, heparin, leukotrienes, prostaglandins, cytokines, nitrogen monoxide or reactive oxygen-containing species.

In certain instances, such as for example sensitive skins, the entire mechanism is also under the control of sensitive nerve endings which release neuropeptides, especially substance P and the peptide derived from calcitonin (designated as Calcitonin Gene Related Peptide or CGRP).

The present invention thus seeks to provide the widest possible beneficial effect in the treatment of all of these skin conditions and therefore provides compositions which acts on several components of these conditions.

Thus, in another embodiment of the present invention compositions are provided which contain, in a physiologically acceptable medium, at least one extract of at least one plant of the Rosaceae family and at least one compound or active species reducing the synthesis, release and/or activity of at least one inflammation mediator.

Preferably, the extract of at least one plant of the Rosaceae family is an extract as described above.

The substrate reducing the synthesis, release and/or activity of at least one inflammation mediator is preferably selected from among substance P and/or CGRP antagonists, NO-synthase inhibitors, bradykinin antagonists, antagonists of cytokines, histamine antagonists, antagonists of type a tumor necrosis factor (TNFα).

Preferably, receptor antagonists are employed.

For example, according to the invention it is possible to incorporate one or more substance P antagonists selected from among peptides, nonpeptide compounds such as those comprising at least one heterocycle, nitrogen-containing compounds comprising at least one benzene ring, salts of monovalent, divalent and trivalent cations, thermal waters, plant extracts, microbial, particularly bacterial, extracts, and mixtures thereof.

Sendide and spantide II are representative substance P-antagonizing peptides according to the invention.

Sendide has the formula:

Tyr-D-Phe Phe D-His Leu Met NH$_2$ in which:

Tyr represents tyrosine,

D-Phe represents D-phenylalanine

Phe represents phenylalanine

D-His represents D-histidine,

Leu represents leucine

Met represents methionine.

Spantide II has the formula:

D-NicLys Pro 3-Pal Pro D-Cl$_2$Phe Asn D-Trp Phe D-Trp Leu Nle NH$_2$ in which:

D-NicLys represents D-lysine nicotinate,

Pro represents proline,

3-Pal represents 3-pyridyl-alanine,

D-Cl$_2$Phe represents D-dichlorophenylalanine,

Asn represents asparagine,

D-Trp represents D-tryptophan

Phe represents phenylalanine,

Leu represents leucine,

Nle represents norleucine.

Other representative substance P-antagonizing peptides include the peptides described in U.S. Pat. No. 4,472,305, U.S. Pat. No. 4,839,465, EP-A-101929, EP-A-333174, EP-A-336230, EP-A-394989, EP-A-443132, EP-A-498069, EP-A-515681, EP-A-517589, WO-A-92/22569 and GB-A-2216529.

The non-peptide substance P antagonists according to the invention are especially compounds comprising a heteroatom bonded directly or indirectly to a benzene ring, or contained in a heterocycle. In particular, such heteroatom is an oxygen, nitrogen or sulfur atom.

Exemplary such heterocyclic compounds according to the invention are those described in: EP-A-360390, EP-A-429366, EP-A-430771, EP-A-499313, EP-A-514273, EP-A-514274, EP-A-514275, EP-A-514276, EP-A-520555, EP-A-528495, EP-A-532456, EP-A-545478, EP-A-558156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116.

In particular, the compound comprising at least one nitrogen-containing heterocycle is a 2-tricyclyl-2-aminoethane derivative, a spirolactam derivative, a quinuclidine derivative, an azacyclic derivative, an aminopyrrolidine derivative, a piperidine derivative, an aminoazaheterocycle or an isoindole derivative.

And other such heterocyclic compounds, include oxygen-containing or sulfur-containing heterocyclic compounds such as furan derivatives, benzofuran derivatives, thiophene derivatives and benzothiophene derivatives, optionally comprising nitrogen-containing substituents, such as the heterocyclic compounds described in U.S. Pat. No. 4,931,459, U.S. Pat. No. 4,910,317 and EP-A-299457, and more especially the alkoxy- and/or aryloxy-tetrazolyl-benzofuran-carboxamides or alkoxy- and/or aryloxy-tetrazolyl-benzothiophene-carboxamides.

Exemplary compounds comprising a nitrogen atom bonded directly or indirectly to a benzene ring, include those described in EP-A-522808, WO-A-93/01165 and WO-A-93/10073.

The salts of cations which are suitable according to the invention are, especially, the salts of strontium, magnesium, lanthanides of atomic number ranging from 57 to 71, cobalt, nickel, manganese, barium, yttrium, copper, tin, rubidium, lithium and zinc.

These salts may, for example, be carbonates, salicylates, bicarbonates, sulfates, glycerophosphates, borates, chlorides, nitrates, acetates, hydroxides, persulfates as well as salts of α-hydroxy acids (citrates, tartrates, lactates, malates) or of fruit acids, or, alternatively, salts of amino acids (aspartate, arginate, glycocholate, fumarate) or salts of fatty acids (palmitate, oleate, caseinate, behenate). Preferably, the salt is selected from among strontium, manganese, yttrium or magnesium nitrate, strontium, manganese, yttrium or magnesium borate, strontium, manganese or magnesium chloride, magnesium, manganese or strontium sulfate. Even more preferably, these salts are strontium chloride or nitrate.

Among the thermal waters which are suitable according to the invention, particularly useful are the thermal waters of the Vichy basin, such as those derived from the Celestins, Chomel, Grande-Grille, Hôpital, Lucas and Parc springs. Preferably, water from the Lucas spring is used.

Exemplary plant extracts according to the invention are particularly the extracts prepared from plants of the Iridaceae family, such as those described in EP-A-0765668.

And exemplary microbial extracts according to the invention include, particularly, the extracts prepared from non-photosynthetic filamentous bacteria such as those described in EP-A-0761204.

The substance P antagonists may be used either alone or as a mixture thereof.

By "CGRP antagonist" is intended any species capable of inhibiting partially or even completely the biological effect of CGRP.

In particular, for a substrate to be recognized as a CGRP antagonist, it should induce a coherent pharmacological response (including or otherwise its attachment to the CGRP receptor) especially in at least one of the following tests:

(a) the antagonist substance should reduce the vasodilation induced by capsaicin and/or by an antidromic electrical stimulation (applied to an afferent nerve) and/or (b) the antagonist substance should cause inhibition of the release of CGRP by the sensitive nerve fibers and/or (c) the antagonist substance should of the contraction of the smooth muscle of the vas deferens induced by CGRP.

Among the known CGRP antagonists, exemplary are CGRP 8–37 (sequence of amino acids 8 to 37 of the N-terminal part of CGRP) or the anti-CGRP antibodies.

Also representative are the plant extracts prepared from plants of the Iridaceae family such as those described in EP-A-0765668.

The CGRP antagonists may also be used either alone or as a mixture thereof.

The term "NO-synthase" comprehends a family of enzymes which effect, specifically, the enzymatic catalysis of L-arginine to citrulline, during which catalysis a gaseous mediator having multiple functions, nitrogen monoxide or NO, is produced. Nitrogen monoxide has, by virtue of its structure, an additional electron which makes it extremely chemically reactive. It is well-known that such compounds are dangerous and efforts are made to limit their production as much as possible. Consequently, in the case of nitrogen monoxide, inhibitors of NO-synthase have been widely studied.

Thus, according to the invention, the inhibitors of NO-synthase are products which make it possible in situ, in humans, to inhibit partially or even completely the synthesis of nitrogen monoxide (NO).

These are, therefore, compounds selected from among the compounds inhibiting the synthesis and/or accelerating the catabolism of NO-synthase, the compounds neutralizing NO-synthase or the compounds which are active in reducing the signal transduced by NO-synthase.

Hence, the inhibitor of NO-synthase may be selected from among optionally modified synthetic or natural peptides, synthetic or natural chemical molecules, antisense nucleic acids, ribozymes, anti-NO-synthase antibodies.

Among these inhibitors of NO-synthase, particularly representative are $N^G$-monomethyl-L-arginine (L-NMMA), $N^G$-nitro-L-arginine, the methylated ester of $N^G$-nitro-L-arginine, diphenyleneiodonium chloride, 7-nitroindazole, N(5)-(1-iminoethyl)-L-ornithine, $N^G,N^G$-dimethyl-L-arginine, $N^G,N^G$-dimethylarginine, 2-(4-carboxyphenyl)-4,4,5,5-tetramethylimidazoline-1-oxy-3-oxide, aminoguanidine, canavanine, ebselen and type a melanocyte-stimulating hormone.

Among the inhibitors of NO-synthase, $N^G$-monomethyl-L-arginine and the type α melanocyte-stimulating hormone are the preferred. The inhibitors of NO-synthase may also be used either alone or as a mixture thereof.

Bradykinin is a peptide of plasma origin which is released from a kininogenic precursor by a plasma protease designated kallikrein (EC 3.4.21.24). This nanopeptide is one of the key mediators of inflammation and has mitogenic properties. The receptors for this kinin can be separated into two principal subtypes B1 and B2. Bradykinin acts especially on the B2 receptor and causes stimulation of numerous systems of production of second messengers, including inositol triphosphates (ip3), known to cause the release of calcium from the intracellular storage sites in the cells including the keratinocyte. Bradykinin also induces the phosphorylation of tyrosine residues through activation of the B2 receptor, depolarization or hyperpolarization of the cell membrane as well as the activation of the metabolism of arachidonic acid.

By "bradykinin antagonist" is intended any compound capable of partially or even completely inhibiting the biological effect of bradykinin.

In particular, for a substrate to be recognized as a bradykinin antagonist, it should induce a coherent pharmacological response including or otherwise its attachment to the bradykinin receptor.

Thus, within this definition is any compound which may interfere with the effects of bradykinin by its attachment to the receptor for the latter (B1 or B2) and/or any compound which, independently of the attachment to the receptor(s), induces by any mechanism an effect which is the opposite of that known for bradykinin (for example, interfering with the synthesis of bradykinin).

Among the bradykinin antagonists, preferred are compounds inhibiting the synthesis and/or accelerating the catabolism of bradykinin, compounds neutralizing bradykinin, compounds blocking the bradykinin receptors such as those which interfere with the effects of bradykinin by their attachment to the receptor for the latter (B1 or B2), compounds inhibiting the synthesis of the receptors for bradykinin or compounds which are active in decreasing the signal transduced by bradykinin. These compounds may be of natural or synthetic origin.

Among the bradykinin antagonists, more particularly representative are the optionally modified synthetic or natural peptides such as D-Arg, [Hyp3, D-Phe7]-bradykinin (NPC567), [Thi 5, 8, D-Phe7]-bradykinin, D-Arg, [Hyp3, Thi5,8, D-Phe7]-bradykinin, N-α-adamantaneacetyl-D-Arg, [Hyp3, Thi5,8, D-Phe7]-bradykinin, des-Arg9, [Leu8]-bradykinin (all sold by the company Sigma) or, alternatively, compounds described in WO-95/08566, WO-95/07294, EP-0623350, EP-0622361, WO-94/11021, EP-0596406, WO-94/06453, WO-94/09001, EP-0578521, EP-0564972, EP-0552106, WO-93/11789, U.S. Pat. No. 5,216,165, U.S. Pat. No. 5,212,182, WO-92/17201, EP-0496369, EP-0472220, EP-0455133, WO-91/09055, WO-91/02746, EP-0413277, EP-0370453, EP-0359310, WO-90/03980, WO-89/09231, WO-89/09230, WO-89/01780, EP-0334244, EP-0596406, WO-86/07263 or P-guanidobenzoyl, [Hyp3, Thi5,D-Tic7,Oic8]-bradykinin (S 16118) (Feletou M & al., *Pharmacol. Exp. Ther.*, June 1995, 273, 1078–84), D-Arg, [Hyp3, Thi5, D-Tic7,Oic8]-bradykinin (HOE 140) (Feletou M & al., *Eur. J. Pharmacol*, 1995, 274, 57–64), D-Arg-[Hyp3, D-Hype (trans-propyl) 7, Oic8]-bradykinin (NPC 17731) (Herzig M. C. S. and Leeb-Lundberg L. M. F., *J. Biol. Chem.* 1995, 270, 20591–20598) or those indicated in "Bradykinin Antagonists: development and applications" (Stewart J. M., *Biopolymers*, 1995, 37, 143–155), or, alternatively, synthetic or natural chemical molecules such as, for example, those described in Salvino et al., *J. Med. Chem.*, 1993, 36, 2583–2584.

Also intended, according to the invention, are antisense nucleic acids or ribozymes whose role is to inhibit selectively the synthesis of bradykinin. These antisense nucleic acids are known to this art. They may act variously on the DNA or messenger RNA coding for bradykinin, especially by blocking the attachment or the progression of the ribosomes along the messenger RNA, by cleaving the messenger RNA with RNase H, or by preventing the transport of messenger RNA from the nucleus to the cytoplasm or by preventing the maturation of the messenger RNA.

Also intended are anti-bradykinin antibodies or soluble receptors for bradykinin, anti-bradykinin receptor antibodies or antagonists of bradykinin receptors.

Preferably according to the invention, a compound is used which interferes with the effects of bradykinin by its attachment to the receptor for the latter (B1 or B2), preferably to the B2 receptor.

Even more preferably, a bradykinin antagonist is used selected from among:

D-Arg, [Hyp3, D-Phe7]-bradykinin (NPC567),

[Thi 5, 8, D-Phe7]-bradykinin, D-Arg, [Hyp3, Thi5,8, D-Phe7]-bradykinin,

N-α-adamantaneacetyl-D-Arg, [Hyp3, Thi5,8, D-Phe7]-bradykinin, des-Arg9, [Leu8]-bradykinin, P-guanidobenzoyl, [Hyp3,Thi5,D-Tic7,Oic8]-bradykinin (S 16118), D-Arg, [Hyp3, Thi5, D-Tic7,Oic8]-bradykinin (HOE 140), D-Arg, [Hyp3, D-Hype (trans-propyl)7, Oic8]-bradykinin (NPC 17731)

The modified peptide that is the preferred according to the invention is D-Arg, [Hyp3, Thi5, D-Tic7,Oic8]-bradykinin (HOE 140).

The bradykinin antagonists may also be used either alone or as a mixture thereof.

It too is known that the substance P released by the sensitive epidermal endings induces a cascade of biochemical events, of which the first steps exist at the level of the mastocytes. The attachment of substance P to the mastocyte receptors induces a release of numerous proinflammatory mediators, among which are histamine, cytokines such as interleukin-1 (IL-1), interleukin-6 (IL-6), interleukin-8 (IL-8) and type a tumor necrosis factor (Tumour Necrosis Factor α (TNF-α)).

By "antagonists of histamine, cytokines and/or TNF-α" are intended any substance capable of inhibiting the release and/or the synthesis and/or the receptor attachment of histamine, cytokines and/or TNF-α, respectively.

The antagonists inhibiting the receptor attachment of histamine are agents specific for the type 1 receptor for histamine (H1).

For a substance to be recognized as a receptor antagonist of histamine, cytokines or TNF-α, it should exhibit one of the following characteristics:

(a) have an affinity for the receptors specific for these compounds;

(b) have a histamine, cytokine or TNF-α receptor antagonist pharmacological activity, namely, induce a coherent pharmacological response in at least one of the following tests:

(i) for the receptor antagonists of histamine: inhibition of the contraction of the smooth muscles which is induced by the administration of histamine;

(ii) for the receptor antagonists of cytokines; inhibition of adhesion of macrophages which is induced by the cytokines on endothelial cells or inhibition of the release of superoxide anions which is induced by the cytokines on the neutrophils;

(iii) for the receptor antagonists of TNF-α: inhibition of the adhesion of macrophages which is induced by TNF-α on the endothelial cells or inhibition of the release of superoxide anions which is induced by TNF-α on the neutrophils or inhibition of the mitogenic activity of TNF-α on the fibroblasts of the dermis.

For a substance to be recognized as an antagonist of the release and/or synthesis of histamine, cytokines or TNF-α, it should exhibit at least one of the following characteristics:

(a) inhibition of the release of histamine by mastocytes stimulated by the compound 48/80 or stimulated by a calcium ionophore (A23 187)

(b) inhibition of the release of cytokines or TNF-α by monocytes (U937 cells) differentiated by a phorbol ester (PMA).

The receptor antagonists of histamine H1 which are suitable according to the invention are those conventionally administered in the treatments of allergic and anaphylactic conditions as well as those for combating travel sickness. Exemplary such compounds include diethylenediamine derivatives such as cinnarizine or cyclizine; aminopropane derivatives such as dexchlorpheniramine, tripolidine; phenothiazine derivatives such as promethazine, alimemazine, as well as the compounds indicated on pages 116 to 118 of the book Joseph R. Prous, *The Year's Drug News*, Therapeutic Targets, 1994 edition, Prous Science Publishers, such as cetirizine-HCl, ebastine, loratadine, setastine-HCl.

The inhibitors of histamine release are especially oxygen-containing or sulfur-containing heterocyclic compounds such as furan derivatives, benzofuran derivatives, thiophene derivatives and benzothiophene derivatives, optionally comprising nitrogen-containing substituents, such as those described in U.S. Pat. No. 4,931,459, U.S. Pat. No. 4,910,317 and EP-A-299457, and, more especially, alkoxy- and/or aryloxy-tetrazol-yl-benzofuran-carboxamides or alkoxy-and/or aryloxy-tetrazol-yl-benzothiophene-carboxamides. Representative are 5-methoxy-3-phenoxy-N-1H-tetrazol-5-yl-benzothiophene-2-carboxamide, 5-methoxy-3-(1-methylethoxy)-N-1H-tetrazol-5-yl-benzothiophene-2-carboxamide, 6-methoxy-3-(1-methylethoxy)-N-1H-tetrazol-5-yl-benzothiophene- 2-carboxamide, 5-methoxy-3-(1-methylethyl)-N-1H-tetrazol-5-yl-benzothiophene-2-carboxamide, 3-benzyloxy-5-methoxy-N-1H-tetrazol-5-yl-benzothiophene-2-carboxamide, and 5-methoxy-3-phenoxy-N-1H-tetrazol-5-yl-benzothiophene-2-carboxamide.

Among the antagonists of cytokines, exemplary are antagonists of the release of interleukin-1 according to the invention, which may be auranofin or SKF-105809 or the tripeptide Lys-Pro-Val or an antagonist of the synthesis of interleukin-1 which may be lactoferin.

The receptor antagonists of TNF-α and the inhibitors of the release and/or of the synthesis of TNF-α which are suitable according to the invention are, in particular, lisophyline, A802715, sulfasalazine.

The antagonists of histamine, cytokines and TNF-α may be synthesized or extracted from naturally occurring substrates (plants or animals).

The antagonists of histamine, cytokines and TNF-α may also be used separately or combined, alone or as a mixture thereof.

The amount of compound reducing the synthesis, release and/or activity of at least one inflammation mediator, formulated into the compositions of the invention of course depends on the desired effect and may therefore vary widely.

To provide an order of magnitude, the compositions of the invention advantageously contain a compound reducing the synthesis, release and/or activity of at least one inflammation mediator in an amount representing from 0.001% to 10% of the total weight of the composition and, preferably, in an amount representing from 0.01% to 5% of the total weight of the composition.

Regardless of the form of the compositions according to the invention, the Rosacea extract is an extract as described above.

According to the invention, the subject compositions may be compositions for cosmetic or pharmaceutical indications. Preferably, the composition is a composition for cosmetic application.

Regardless of the form of the composition according to the invention in which at least one extract of at least one plant of the Rosaceae family is formulated, it may be ingested, injected or topically applied to the skin (over any skin region of the body), the hair, the nails or the mucous membranes (buccal, jugal, gingival, genital, conjunctiva). Depending on the mode of administration, the composition according to the invention may be provided in any of the galenic forms conventional to this art.

For topical application onto the skin, the composition is advantageously in the form of an aqueous or oily solution or of a dispersion of the lotion or serum type, of emulsions of liquid or semiliquid consistency of the milk type, which are obtained by dispersing a fatty phase in an aqueous phase (O/W) or conversely (W/O), or of suspensions or emulsions of soft consistency of the aqueous or anhydrous cream or gel type, or, alternatively, of microcapsules or microparticles, or of vesicular dispersions of the ionic and/or nonionic type. These compositions are formulated according to the usual techniques.

They may also be applied to the hair in the form of aqueous, alcoholic or aqueous/alcoholic solutions, or in the form of creams, gels, emulsions, foams, or, alternatively, in the form of compositions for aerosol also comprising a pressurized propelling agent.

For administration by injection, the composition may be provided in the form of an aqueous or oily lotion or in the form of a serum. For the eyes, it may be provided in the form of drops, and for ingestion, it may be provided in the form of capsules, granules, syrups or tablets.

The amounts of the various constituents of the compositions according to the invention are those conventional to the particular art under consideration.

The subject compositions are advantageously formulated as creams for cleansing, protecting, treating or caring for the face, for the hands, for the feet, for the large anatomical skin-folds or for the body, (for example day creams, night creams, makeup removing creams, foundation creams, anti-sun (sunscreen) creams), fluid foundations, makeup removing milks, body protecting or care milks, antisun (sunscreen) milks, skin-care lotions, gels or foams, such as cleansing lotions, antisun (sunscreen) lotions, artificial tanning lotions, bath compositions, deodorant compositions comprising a bactericidal agent, aftershave gels or lotions, depilatory creams, compositions for combating insect bites, analgesic compositions, compositions for treating certain skin diseases such as eczema, rosacea, psoriasis, lichens, severe pruritus, etc.

The compositions according to the invention may also be formulated as solid preparations constituting cleansing cakes or soaps.

The subject compositions may also be packaged in the form of a composition for an aerosol also comprising a pressurized propelling agent.

The compositions according to the invention may also be formulated for hair care, and especially as a shampoo, a hair setting lotion, a treatment lotion, a hair styling gel or cream, a dyeing composition (especially oxidation dyes) optionally in the form of coloring shampoos, restructuring lotions for the hair, a permanent-waving composition (especially a composition for the first stage of a permanent waving), a lotion or gel for preventing hair loss, an antiparasitic shampoo and the like.

The subject compositions may also be for dentibuccal use, for example a toothpaste. In this instance, the composition may contain customary adjuvants and additives for buccal use and especially surfactants, thickeners, humectants, polishing agents such as silica, various active ingredients such as fluorides, in particular sodium fluoride, and optionally sweeteners such as sodium saccharinate.

When the composition is an emulsion, the proportion of the fatty phase advantageously ranges from 5% to 80% by weight, and preferably from 5% to 50% by weight relative to the total weight of the composition. The oils, waxes, emulsifiers and coemulsifiers formulated into the composition in the form of an emulsion are selected from among those conventional in the cosmetic field.

The emulsifier and coemulsifier are advantageously present in the composition in a proportion ranging from 0.3% to 30% by weight, and preferably from 0.5 to 20% by weight relative to the total weight of the composition. The emulsion may, in addition, contain lipid vesicles.

When the composition is an oily gel or solution, the fatty phase may constitute more than 90% of the total weight of the composition.

In known fashion, the cosmetic compositions may also contain the usual adjuvants and additives in the cosmetic field, such as hydrophilic or lipophilic gelling agents, hydrophilic or lipophilic additives, preservatives, antioxidants, solvents, perfumes, fillers, screening agents, odor absorbers and colorants. The amounts of these various adjuvants and additives are those which are conventional in the cosmetic field, and range, for example, from 0.01% to 10% of the total weight of the composition. These adjuvants and additives, depending on their nature, may be incorporated into the fatty phase, into the aqueous phase and/or into the lipid spherules.

Exemplary oils or waxes according to the invention, include the mineral oils (petroleum jelly), vegetable oils (liquid fraction of shea butter, sunflower oil), animal oils (perhydrosqualene), synthetic oils (purcellin oil), silicone oils or waxes (cyclomethicone) and fluorinated oils (perfluoropolyethers), beeswax, carnauba wax or paraffin. Fatty alcohols and fatty acids (stearic acid) may be added to these oils.

Exemplary emulsifiers according to the invention include glycerol stearate, polysorbate 60 and the PEG-6/PEG-32/Glycol Stearate mixture marketed under the trademark Tefose® 63 by Gattefosse.

Exemplary solvents according to the invention include the lower alcohols, especially ethanol and isopropanol, propylene glycol.

And exemplary hydrophilic gelling agents according to the invention include carboxyvinyl polymers (carbomer), acrylic copolymers such as acrylate/alkylacrylate copolymers, polyacrylamides, polysaccharides such as hydroxypropyl cellulose, naturally occurring gums and clays, and, representative lipophilic gelling agents include modified clays such as bentones, metal salts of fatty acids such as aluminim stearates and hydrophobic silica, ethyl cellulose, polyethylene.

The subject compositions may contain other hydrophilic active agents such as proteins or protein hydrolysates, amino acids, polyols, urea, allantoin, sugars and sugar derivatives, water-soluble vitamins, plant extracts and hydroxy acids.

Exemplary such lipophilic active agents include retinol (vitamin A) and derivatives thereof, tocopherol (vitamin E) and derivatives thereof, essential fatty acids, ceramides, essential oils, salicylic acid and derivatives thereof.

The compositions of the present invention may contain, together with the at least one extract of at least one plant of the Rosaceae family, other active agents especially suitable for the prevention and/or treatment of a variety of skin conditions. Exemplary such "other" active agents include:

(a) agents modulating skin pigmentation and/or proliferation and/or differentiation such as retinoic acid and isomers hereof, retinol and esters thereof, vitamin D and derivatives thereof, estrogens such as estradiol, kojic acid or hydroquinone;

(b) antibacterial agents such as clindamycin phosphate, erythromycin or antibiotics of the class of tetracyclines;

(c) antiparasitic agents, in particular metronidazole, crotamiton or pyrethrinoids;

(d) antifungal agents, in particular the compounds belonging to the class of imidazoles such as econazole, ketoconazole or miconazole or their salts, polyene compounds, such as amphotericin B, compounds of the family of allylamines, such as terbinafin, or alternatively octopirox;

(e) antiviral agents such as acyclovir;

(f) steroidal anti-inflammatory agents, such as hydrocortisone, betamethasone valerate, clobetasol propionate, or nonsteroidal anti-inflammatory agents such as ibuprofen and its salts, diclofenac and its salts, acetylsalicylic acid, acetaminophen or glycyrrhetinic acid;

(g) anaesthetic agents such as lidocaine hydrochloride and derivatives thereof;

(h) antipruriginous agents such as thenaldine, trimeprazine or cyproheptadine;

(i) keratolytic agents such as alpha- and beta-hydroxycarboxylic or beta-ketocarboxylic acids, their salts, amides or esters and more particularly hydroxy acids such as glycolic acid, lactic acid, salicylic acid, citric acid and in general fruit acids, and 5-n-octanylsalicylic acid;

(j) anti-free radical agents, such as alpha-tocopherol or its esters, superoxide dismutases, some metal chelators or ascorbic acid and its esters;

(k) antiseborrhoeic agents such as progesterone;

(l) antidandruff agents such as octopirox or zinc pyrithione;

(m) antiacne agents such as retinoic acid or benzoyl peroxide;

(n) plant extracts or extracts of microbial origin.

In order to further illustrate the present invention and the advantages thereof, the following specific examples are given, it being understood that same are intended only as illustrative and in nowise limitative.

In said examples to follow, all parts and percentages are given by weight, unless indicated otherwise.

EXAMPLE 1

Biological Activity of a *Rosa gallica* Extract

The receptor affinity of the extract of petals of at least one plant of the Rosaceae family was measured for the human NK1 receptor (human substance P receptor):

(1) The measurement of the receptor affinity of the extract of petals of at least one plant of the Rosaceae family for the human NK1 receptor was carried out according to the technique described in the article: Heuillet, E. et al, *J. Neurochem.*, 60, 868–876 (1993).

The extract was tested at the concentrations of 1%, 5% and 10% and was a *Rosa gallica* extract marketed under the trademark Herbasol® by COSMETOCHEM.

During each experiment, the reference molecule for the receptor studied ([Sar$^9$, Met (0$_2$)$^{11}$] SP, a substance P analogue described by Heuillet, E. (Heuillet, E. et al, *J. Neurochem.*, 60, 1993, 868–876)) was tested in parallel at eight (8) concentrations (n=2) in order to provide a standard curve permitting the experiment to be validated.

There were thus obtained:

53% attachment for the extract of Example 1 at 1%

90% attachment for the extract of Example 1 at 5%

96% attachment for the extract of Example 1 at 10%

The results of this experiment demonstrated affinity of the extract for the human substance P receptor from the concentration of 1%.

The affinity curve plotted from the results obtained evidenced 50% displacement of the natural ligand (IC$_{50}$) by the extract at the concentration of 2%.

(2) A functional test in vitro carried out on the human NK1 receptor (human substance P receptor) present on the smooth muscles of isolated intestine (ileum) was carried out in order to demonstrate the substance P-antagonizing nature of the extract.

The in vitro experiments were carried out according to the technique described by Dion et al. (*Life Sciences*, 41, 1987, 2269–2278) and Patacchini et al. (*Eur. J. Pharmacol.*, 215, 1992, 93–98).

After establishment in experimental tanks, the tissues (smooth muscles) were subjected to an initial tension of 1 g. An equilibration period of at least 60 minutes, during which the physiological solution was replaced several times and the initial tension readjusted, was then observed before adding the extract.

The experiments were carried out in the continuous presence of atropine ($3 \times 10^{-6}$ M) of pyrilamine ($3 \times 10^{-6}$ M) and of indomethacin ($10^{-6}$ M) in order to eliminate the indirect effects of mediators used during the stimulation of other types of receptors present on this tissue.

Each preparation was initially stimulated by a substance P agonist: [Sar$^9$, Met (0$_2$)$^{11}$ SP], at the concentration of $10^{-8}$ M in order to obtain a "control" contractile response, and then the physiological solution was completely renewed.

This operation was then repeated every 40 minutes in the presence of increasing concentrations of the extract of petals of at least one plant of the Rosaceae family, each of these being added 30 minutes before the [Sar$^9$, Met (0$_2$)$^{11}$ SP].

A 50% inhibition of the activity of [Sar$^9$, Met (0$_2$)$^{11}$ SP] was attained at the extract concentration of 1%.

Conclusions:

The extract had affinity for the substance P receptor and exerted a substance P-antagonizing specific activity.

EXAMPLE 2

Specific examples of formulations according to the invention, and particularly those compositions containing at least one extract of petals of at least one plant of the Rosaceae family together with an active species eliciting an irritant effect, are set forth below. These compositions were formulated simply by intimately admixing the various constituents thereof.

| Composition 1: Makeup removing lotion for the face | |
|---|---|
| Herbasol ® | 1.00 |
| Antioxidant | 0.05 |
| Isopropanol | 40.00 |
| Preservative | 0.30 |
| Water | qs 100% |

| Composition 2: Face-care gel | |
|---|---|
| Herbasol ® | 4.00 |
| Hydroxypropyl cellulose* | 1.00 |
| Antioxidant | 0.05 |
| Isopropanol | 40.00 |
| Preservative | 0.30 |
| Water | qs 100% |

| Composition 3: Face-care cream (oil-in-water emulsion) | |
|---|---|
| Herbasol ® | 5.00 |
| Glycerol stearate | 2.00 |
| Polysorbate 60** | 1.00 |
| Stearic acid | 1.40 |
| Triethanolamine | 0.70 |
| Carbomer | 0.40 |
| Liquid fraction of shea butter | 12.00 |
| Perhydrosqualene | 12.00 |
| Antioxidant | 0.05 |
| Perfume | 0.50 |
| Preservative | 0.30 |
| Water | qs 100% |

| Composition 4: Shampoo | |
|---|---|
| Herbasol ® | 2.00 |
| Hydroxypropyl cellulose* | 1.00 |
| Perfume | 0.50 |
| Preservative | 0.30 |
| Water | qs 100% |

| Composition 5: Antiwrinkle care cream for the face (oil/water emulsion) | |
|---|---|
| Herbasol ® | 6.00 |
| Glycerol stearate | 2.00 |
| Polysorbate 60** | 1.00 |
| Stearic aaid | 1.40 |
| 5-n-Octanylsalicylic acid | 0.50 |
| Triethanolamine | 0.70 |
| Carbomer | 0.40 |
| Liquid fraction of shea butter | 12.00 |
| Perhydrosqualene | 12.00 |
| Antioxidant | 0.05 |
| Perfume | 0.5 |
| Preservative | 0.30 |
| Water | qs 100% |

| Composition 6: Analgesic gel | |
|---|---|
| Herbasol ® | 10.00 |
| Hydroxypropyl cellulose* | 1.00 |
| Antioxidant | 0.05 |
| Lidocaine hydrochloride | 2.00 |
| Isopropanol | 40.00 |
| Preservative | 0.30 |
| Water | qs 100% |

| Composition 7: Solar erythema care cream (oil-in-water emulsion) | |
|---|---|
| Herbasol ® | 2.00 |
| Glycerol stearate | 2.00 |
| Polysorbate 60** | 1.00 |
| Stearic acid | 1.40 |
| Glycyrrhetinic aaid | 2.00 |
| Triethanolamine | 0.70 |
| Carbomer | 0.40 |
| Liquid fraction of shea butter | 12.00 |
| Sunflower oil | 10.00 |
| Antioxidant | 0.05 |
| Perfume | 0.5 |
| Preservative | 0.30 |
| Water | qs 100% |

| Composition 8: Gel for the treatment of acne | |
|---|---|
| Herbasol ® | 8.00 |
| All-trans-retinoic acid | 0.05 |
| Hydroxypropyl cellulose* | 1.00 |
| Antioxidant | 0.05 |
| Isopropanol | 40.00 |
| Preservative | 0.30 |
| Water | qs 100% |

| Composition 9: Lotion for removing scars due to acne | |
|---|---|
| Herbasol ® | 2.50 |
| Glycolic acid | 50.00 |
| Hydroxypropyl cellulose* | 0.05 |
| NaOH | qs pH = 2.8 |
| Ethanol | qs 100% |
| Preservative | 0.30 |

*: Klucel H ® marketed by Hercules
**: Tween 60 ® marketed by ICI

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. The method for therapeutically treating a disease state, disorder, condition or affliction entailing an excessive synthesis and/or release of substance P, comprising administering to an individual subject in need of such treatment, an effective substance P antagonist amount of at least one extract of at least one plant of the Rosaceae family.

2. The method as defined by claim 1, comprising therapeutically treating a skin disorder, inflammation, an allergic syndrome, pain, a collagen maturation disorder, a disorder of the central nervous system, a respiratory disorder, a gastrointestinal disorder, fibroses, a cardiovascular disorder, a vasospastic disorder, an immunological disorder or disorder of the urinary tract, rheumatic disease and/or an ophthalmological condition.

3. The method as defined by claim 1, comprising therapeutically treating sensitive skin.

4. The method as defined by claim 1, comprising therapeutically preventing and/or combating skin irritation and/or dartres and/or erythemas and/or sensations of inflammation and/or of dysaesthesia and/or pruritus of the skin and/or the mucous membranes.

5. The method as defined by claim 1, said at least one extract of at least one plant of the Rosaceae family having been derived from a whole plant, or from the leaves, stems, flowers, petals, root or undifferentiated cells thereof.

6. The method as defined by claim 5, said at least one extract of at least one plant of the Rosaceae family having been derived from the petals thereof.

7. The method as defined by claim 5, said at least one extract being obtained from at least one plant of the Rosaceae family that has been cultured in vivo.

8. The method as defined by claim 1, said at least one extract being obtained from at least one plant of the Rosaceae family of genera, Agrimonia, Amygdalus, Armeniaca, Cerasus, Malus, Mespilus, Persica, Pirus, Prunus, Rosa and/or Rubus.

9. The method as defined by claim 8, said at least one extract being obtained from at least one plant of the Rosaceae family genus, Rosa.

10. The method as defined by claim 9, said at least one extract being obtained from at least one plant of the Rosa genus, comprising at least one of the species *Rosa alba, Rosa alpina, Rosa canina, Rosa cinnamonea, Rosa gallica, Rosa repens, Rosa rubrifolia, Rosa rubiginosa, Rosa sempervirens, Rosa spinosissima, Rosa stylosa, Rosa tomentosa* and/or *Rosa villosa*.

11. The method as defined by claim 10, said at least one species comprising *Rosa gallica*.

* * * * *